United States Patent [19]
Lee

[11] Patent Number: 4,768,502
[45] Date of Patent: Sep. 6, 1988

[54] PERFORATED SPLINT

[76] Inventor: Lawrence L. Lee, 3776 Martha St., San Diego, Calif. 92117

[21] Appl. No.: 832,589

[22] Filed: Feb. 25, 1986

Related U.S. Application Data

[63] Continuation-in-part of Ser. No. 707,865, Mar. 4, 1985.

[51] Int. Cl.$^4$ ................................................. A61F 5/04
[52] U.S. Cl. ................................. 128/87 A; 128/87 R
[58] Field of Search ..................... 128/89 R, 90, 87 R, 128/87 A, 77, 133, 134, 135

[56] References Cited

U.S. PATENT DOCUMENTS

| | | | |
|---|---|---|---|
| 458,804 | 9/1891 | Ellis | 128/89 R |
| 1,512,558 | 10/1924 | Montgomery | 128/89 R |
| 2,060,001 | 11/1936 | Attwood et al. | 128/89 R |
| 2,070,810 | 2/1937 | Saling | 128/89 R |
| 2,312,523 | 3/1943 | Corbett | 128/85 |
| 3,036,831 | 5/1962 | Engan | 128/89 R |
| 4,169,469 | 10/1979 | Arluck | 128/90 |
| 4,382,439 | 5/1983 | Shen | 128/89 R |

Primary Examiner—Robert A. Hafer
Assistant Examiner—Michael Brown

[57] ABSTRACT

A splint for use with retaining straps to immobilize part of a limb comprising an elongated rigid sheet and a rigid collar. The sheet is formed into a shape to conform to the surface of one side of the part of the limb to be immobilized. The collar, which is attached to one end of the sheet, extends circumferentially more than halfway around the limb, grips the limb, and holds it in a fixed position relative to the sheet. Retaining straps are used at other positions along the sheet to hold the limb against the splint. In one embodiment, the splint is made of stainless steel, the sheet is formed of intersecting strips of stainless steel that are spotwelded together at intersection points to form a perforated sheet having large holes distributed throughout its area for ventilation and removal of water from the surface of the limb. The collar can be attached to the sheet in more than one orientations; one of these orientations allows the splint to fit a person's left limb, and another one of these orientations allows the splint to fit the person's right limb. Final adjustments of the splint are made by manually bending the sheet and the collar. The splint can be made to fit the limb so well that it is comfortable to wear in direct contact with the skin (without padding material) for extended periods of time.

4 Claims, 3 Drawing Sheets

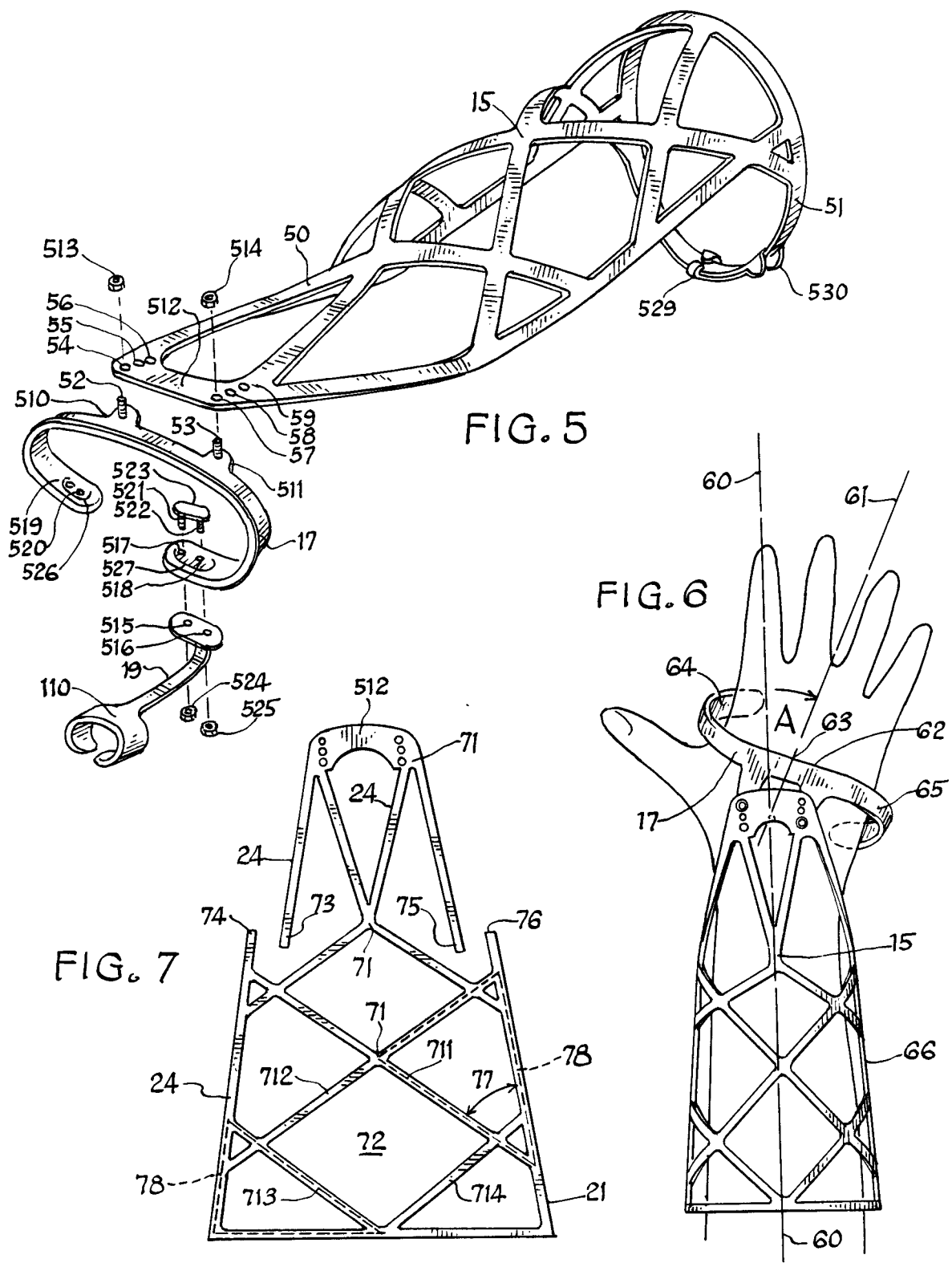

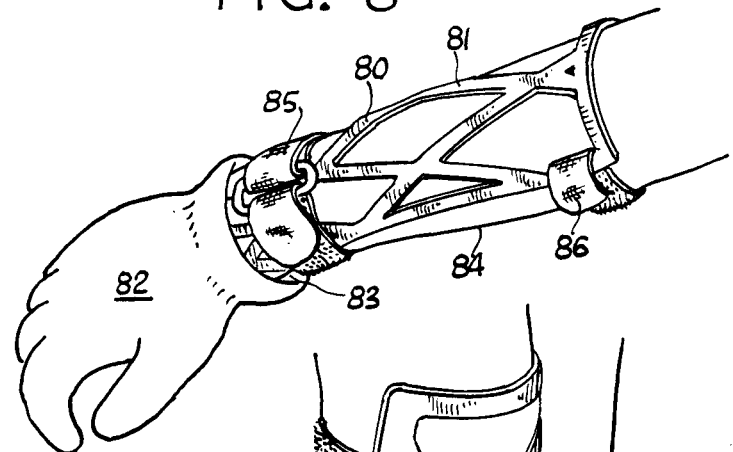
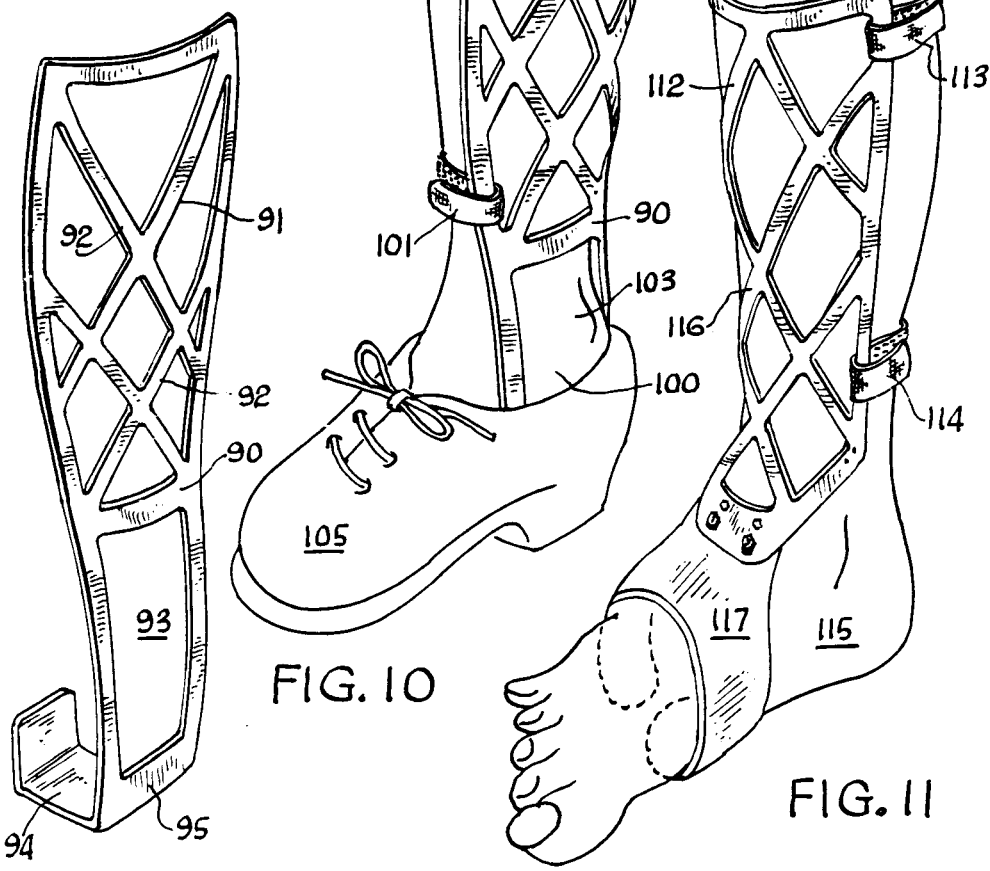

PERFORATED SPLINT

This application is a continuation-in-part of my preceding application Ser. No. 707,865, filed Mar. 4, 1985.

BACKGROUND OF THE INVENTION

This invention relates to apparatus for immobilization of a part of a person's limb. Such apparatus are generally used for orthopedic treatment of limb injuries.

Depending on the nature of the injury, the affected part of the limb may be placed in a cast for a period of time ranging from a few days to many months. The casts that are most commonly used at the present time are made of plaster of paris or plastic with reinforcing fabric. Such casts are usually formed over the patient's limb and they usually include some padding materials to prevent abrasion to the skin on the surfaces of contact. Such casts have the following disadvantages: (1) They do not provide sufficient ventilation for cooling and removal of moisture in warm weather, during active physical exercise, or for limb injuries that include injuries of the skin. (2) If one such cast gets wet, it is very troublesome to dry because the padding materials, which in most cases are thick pads of cotton, absorb water readily. (3) If such a cast gets dirty, it is very difficult to clean. (4) The skin under the cast cannot be cleaned easily, therefore the skin becomes dirty and itchy after a week or so of wearing such a cast. (5) Such a cast is usually so thick that it makes the covered part of the limb uncomfortably hot in warm weather. (6) Such a cast is usually so thick that the patient cannot wear his regular clothes over the cast in cold weather.

It is therefore highly desirable to have an apparatus to perform the function of a cast for immobilization of a part of a limb but not have the disadvantages described above.

There have been several attempts to make such an apparatus; however, most of these attempts resulted in apparatus that cannot be made to fit the limb very comfortably. Therefore, the apparatus can only be used for very short periods of time (such as in the ambulance on the way to the hospital). The ones that can be made more comfortable can only be made to fit a very narrow range of sizes and shapes. Moreover a splint of the latter type that is made for a right limb cannot be used on a left limb, and vice versa. The physician must therefore keep an inventory of many such apparatus to be able to fit most patients.

Some of the apparatus in the prior art have a wire mesh which can be bent into a generally cylindrical shape to fit over some parts of the limb. Examples of such apparatus include a splint described in U.S. Pat. No. 2,060,001 issued to Attwood et al, and a surgical splint described in U.S. Pat. No. 1,512,558 issued to Montgomery. Wire meshes are generally difficult to stretch; so an initially-flat piece of wire mesh can only be bent into shapes such as cylinders and cones, but it cannot be bent into a saddle-shape which is needed to fit comfortably over wrists and ankles.

The wrist and ankle are among the most frequently injured parts of the body. To immobilize a wrist or an ankle, the apparatus must hold the wrist/ankle in a fixed position relative to the parts of the limb in the proximal and distal directions. The part of the limb in the proximal direction is, in both cases, long, relatively insensitive, and easy to hold onto. But in both cases, the part of the limb in the distal direction (the hand, distal from the wrist, and the foot, distal from the ankle) are short, highly sensitive and difficult to immobilize. An apparatus for immobilizing the wrist and ankle must therefore have special provision for a comfortable fit over the hand and the foot. One embodiment of the present invention provides an adjustable collar that enables the apparatus to grasp the hand and the foot comfortably. Other embodiments of the present invention use ordinary clothing materials to help grasp the hand and foot (a glove for the hand, and a shoe for the foot).

It is highly desirable to have an apparatus that
 does not have the disadvantages of the plaster or plastic splints,
 is sufficiently comfortable that the apparatus can be worn over long periods of time,
 can be adjusted to fit limbs over a wide range of sizes and shapes, and
 can be adjusted to fit both the left limb and the right limb.

The present invention provides such an apparatus. This apparatus shall be referred to as a "splint".

SUMMARY OF THE INVENTION

One embodiment of the invention comprises a splint for use with retainer means to immobilize part of a limb. The splint comprises a rigid sheet and a rigid collar. The sheet is formed into a shape to conform to the surface of one side of the part of the limb to be immobilized. The collar, which is attached to one end of the sheet, extends circumferentially more than halfway around the limb, grips the limb, and holds it in a fixed position relative to the sheet. Retainer means are used at other positions along the sheet to hold the splint against the limb. The collar can be attached to the sheet in more than one orientations; one of these orientations allows the splint to fit a person's left limb, and another one of these orientations allows the splint to fit the person's right limb. Final adjustments of the splints are made by manually bending the sheet and the collar until the splint fits the limb comfortably. The sheet is perforated with large holes to facilitate the ventilation and removal of water from the surface of the limb. In one preferred embodiment, the sheet is formed by spotwelding together a number of intersecting stainless steel strips at positions where they intersect.

BRIEF DESCRIPTION OF THE DRAWINGS

FIG. 5 is an exploded view of a splint which is similar to the splint of FIG. 2 except that the splint shown in this figure has an additional proximal collar.

FIG. 6 is a top view of a person's forearm wearing a preferred embodiment of a splint according to the present invention.

FIG. 7 is a plan view of a pattern used in the fabrication of the splint of FIG. 2.

FIG. 8 is a perspective view of a person's forearm wearing a preferred embodiment of a splint which is constructed according to the present invention.

FIG. 9 is a perspective view of a part of another preferred embodiment of a splint which is constructed according to the present invention.

FIG. 10 is a perspective view of a person's lower leg wearing the splint of FIG. 9.

FIG. 11 is a perspective view of a person's lower leg wearing another preferred embodiment of a splint which is constructed according to the present invention.

DETAILED DESCRIPTION OF THE INVENTION

Figure 1:
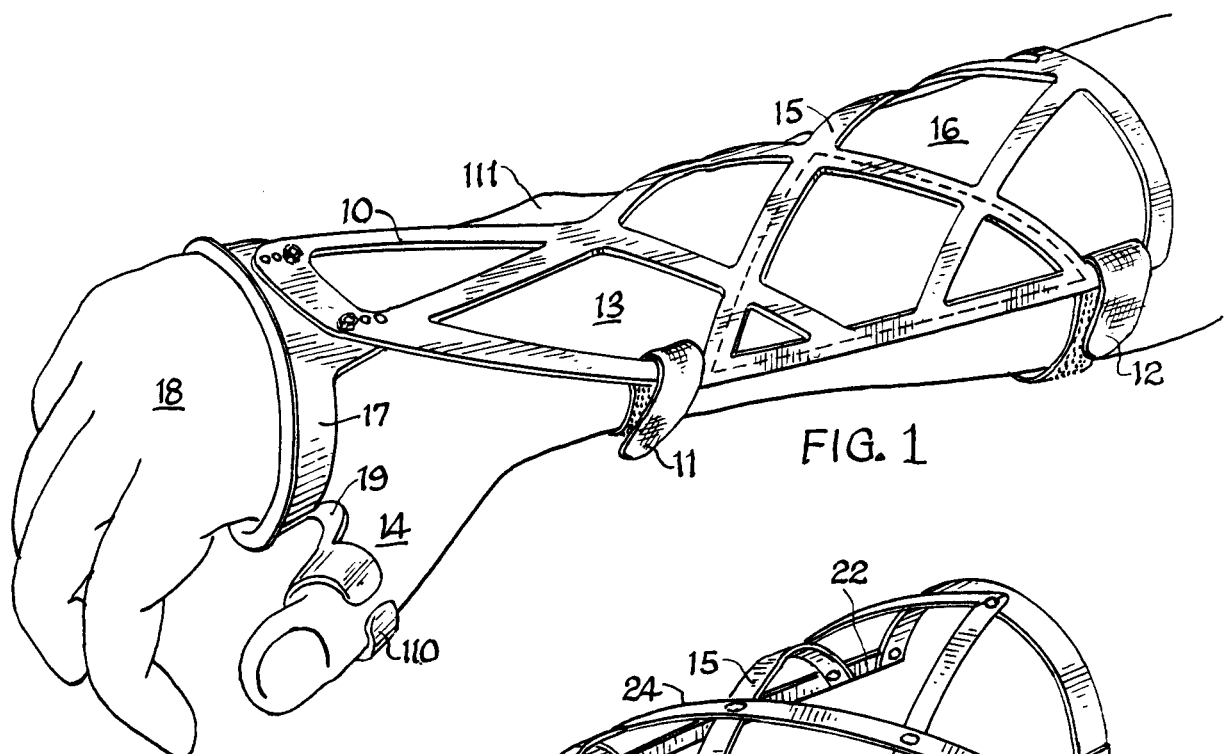
FIG. 1 is a perspective view of a person's forearm wearing the splint of FIG. 2.
Figure 2:
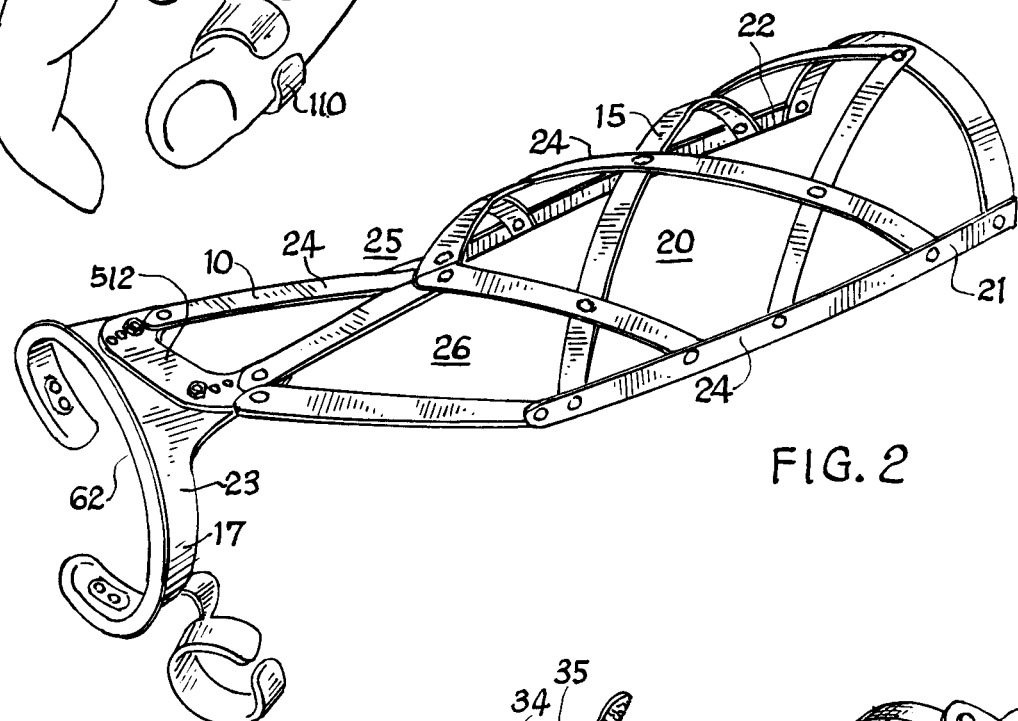
FIG. 2 is a perspective view of a preferred embodiment of a splint which is constructed according to the present invention.

One preferred embodiment of the present invention is shown in FIG. 1 and FIG. 2. In this embodiment, splint 10 is used with retainer means 11 and 12 to immobilize a part of a limb (a wrist 13) and a digit (a thumb 14).

The splint 10 comprises one rigid sheet 15 of metal (in this case stainless steel) formed into a shape to conform to the dorsal side of the forearm 16. Most of the area of this sheet 15 is occupied by large holes 20 for ventilation and removal of water from the surface of the limb. In order for the holes 20 to be considered large enough for convenient removal of water, they should be at least large enough for the insertion of two fingers holding a piece of cotton.

In addition to the sheet 15, the splint 10 also has a rigid collar 17 in the shape of an elongated letter "C" extending circumferentially more than halfway around the hand 18. Collar 17 is rigidly attached to sheet 15. Collar 17 grips the hand 18 to prevent rotation and other lateral motions of the hand 18 relative to the sheet 15.

Optionally, a stem 19, connected to collar 17, extends in the direction of the thumb 14 to a ring 110. The ring 110 is made of a strip of stainless steel and it is connected to stem 19. Ring 110 is bent into almost a full circle to fit around the thumb. The combination of stem 19 and ring 110 prevents lateral motion of the thumb 14 relative to the collar 17.

Figure 3:
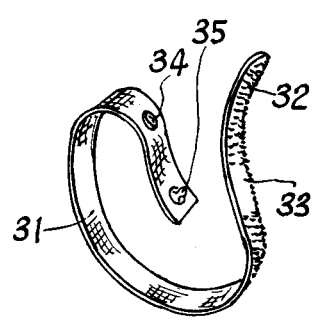
FIG. 3 is a perspective view of a retainer means which is suitable for use with a splint according to the present invention.

The retainer means 11 and 12 of FIG. 1 are shown in more detail in FIG. 3. This retainer means comprises a nylon fabric strap 31 with "Velcro" fasteners 32 (hooks) and 33 (loops) for attaching to an edge 21 of the sheet 15. A snap-fastener 34 and 35 attaches the strap 31 to the other edge 22 of the sheet 15.

Figure 4:
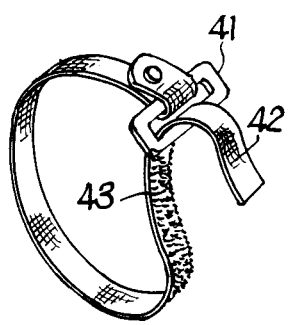
FIG. 4 is a perspective view of another retainer means which is suitable for use with a splint according to the present invention.

Any other retainer means that serves the purpose of holding the wrist 13 and the forearm 16 securely in position against the splint 10 can be used instead of 11 and 12. One such other retainer means is shown in FIG. 4. The retainer means of FIG. 4 is similar to the retainer means of FIG. 3 except it is longer in length and has a buckle 41 at one end through which one part of the "Velcro" fastener 42 is passed before being attached to the other part 43 of the "Velcro" fastener to form a closed loop around the limb and the splint, thereby keeping the splint in contact with the limb.

Further examples of usable retainer means include bandages, watchbands, and sportsmen's wrist protectors.

The wrist 13 is immobilized because, at the proximal end (of the splint), the forearm 16 is held fixed by retainer means 12; at the distal end, the hand is held fixed by collar 17; and in the middle the wrist is held fixed by the retainer means 11. The thumb 14 is immobilized by the ring 110. The sheet 15, collar 17, stem 19 and ring 110 are all sufficiently rigid to provide the desired immobilization.

A similar embodiment of the present invention is shown partly unassembled in FIG. 5. In the drawings, parts that are shown in different figures but are otherwise identical are assigned the same identification number, only parts that are different are assigned different numbers. All parts of the splint 50 are identical to the corresponding parts in splint 10 except splint 50 has an additional collar 51 at the proximal end. Accordingly all parts of splint 50 are assigned the same numbers as the corresponding parts of splint 10 (this includes sheet 15, but not collar 51).

Collar 17 is attached to sheet 15 by means of attachment means 52-59. Attachment means 52 and 53 are screws welded onto tabs 510 and 511 that are in turn welded onto collar 17 and extend laterally away from collar 17 in the direction of sheet 15. Attachment means 54-59 are holes punched into the attachment plate 512 which is located at the distal end of the sheet 15 and is a part of the sheet 15. The holes 54-56 being placed along a row on one side and the holes 57-59 along another row on the other side such that screw 52 can be inserted into any one of the three holes 54-56 while screw 53 is inserted into any one of the three holes 57-59. In the embodiment illustrated in FIGS. 1, 2 and 5, the total number of attachment means is eight.

FIG. 5 shows a screw 52 aligned with a hole 54, and another screw 53 aligned with another hole 57. By inserting these screws 52 and 53 through the holes 54 and 57 respectively, and securing them with nuts 513 and 514, collar 17 is rigidly attached to sheet 15.

There are other ways with which attachment means can be picked two-at-a-time to be fastened together: For example, screw 52 could have been fastened to hole 56 instead of 54, while screw 53 remains fastened to hole 57.

When the collar 17 is attached to the sheet 15 as shown aligned in FIG. 5, the resulting sheet-and-collar part of the splint will be substantially symmetrical about a central plane.

A symmetrical splint is however not always the most desirable because the hand is not symmetrical. To discuss a better-fitting splint configuration, it is useful to refer to FIG. 6. A portion of the sheet 15 (near the proximal end) is in the shape of a part of a cone 66. The axis 60 of this cone is the longitudinal axis 60 of the sheet 15. The orientation of the collar 17 with respect to the sheet 15 is described by an angle A between the longitudinal axis 60 and a normal 61 to a distal edge 62 of the collar 17 at its central position 63. The angle A is positive if the collar is rotated to the right with respect to the symmetrical orientation.

When the collar 17 is attached symmetrically to the sheet 15 as shown aligned in FIG. 5, the resulting splint would have an angle A equal to zero.

If screw 52 were fastened to hole 56, while screw 53 is fastened to hole 57, then the resulting splint will have an angle A approximately equal to +20 degrees.

Each way of picking attachment means 52-59 two-at-a-time to be attached together defines a predetermined orientation for attaching the sheet 15 to the collar 17. For example:

pick a, fasten 53 to 57 and 52 to 54, Angle A=0 degrees pick b, fasten 53 to 59 and 52 to 56, Angle A=0 degrees pick c, fasten 53 to 57 and 52 to 55, Angle A = +10 degrees pick d, fasten 53 to 57 and 52 to 56, Angle A = +20 degrees pick e, fasten 53 to 59 and 52 to 54, Angle A = −20 degrees As shown in the above example, the number of ways in which the attachment means can be picked two-at-a-time is at least five.

Most persons have a right hand oriented at an angle to the right with respect to the forearm. So most right hands are fitted best with splints having positive angles A; whereas most left hands are best fitted with splints having negative angles A. In the preferred embodiment of a splint according to the present invention, angle A can be varied from +20 degrees to −20 degrees which is a sufficient range to fit most hands. The range of this angle can be easily be varied by changing the positions of the attachment means, or by using other attachment means.

FIG. 5 shows stem 19 and ring 110 unassembled from collar 17. A splint according to the present invention can be used without the stem and ring if the thumb need not be immobilized.

The stem 19 and ring 110 can be connected to the collar at either of two positions, one for the left thumb, and the other one for the right thumb.

At the extremity of stem 19 away from ring 110 are two holes 515 and 516 which serve as connecting means for connecting stem 19 and ring 110 to collar 17. These holes 515 and 516 can be aligned with holes 517 and 518 near one end of collar 17. Holes 515 and 516 can also be aligned with holes 519 and 520 near the other end of collar 17. Holes 515–520 are all connecting means, the total number of connecting means being six.

The connecting means 515 and 516 may be aligned with 517 and 518 as shown in FIG. 5 and fastened together with screws and nuts. In the embodiment illustrated in FIG. 5, the screws 521 and 522 are welded onto a bridge 523. Bridge 523 makes connecting easier by preventing rotation of the screw while the nuts 524 and 525 are being tightened.

Indentations 526 and 527 are stamped onto the collar 17 so the bridge 523 will lie flush with the rest of the collar.

There are two ways in which the connecting means can be picked two-at-a-time to be fastened together to give useful results; they are:

pick x, fasten 515 to 517 and 516 to 518, for right thumb and pick y, fasten 515 to 519 and 516 to 520, for left thumb.

The present invention is not limited by the exact positioning of, or the number of, or the type of attachment means, connection means, and fasteners. It is obvious that a functional splint according to the present invention can be made using many different combinations of means for joining together the various interchangeable parts.

In addition to the adjustments provided for by the selection of the attachment means and the connection means, a splint according to the present invention is also adjustable by bending the sheet 15, the collar 17, the stem 19 and/or the ring 110.

At this point, it is elucidative to explain how the splint, which has previously been specified as being "rigid", can be adjusted by bending:

Rigidity of any physical object can only be considered in relative terms because all material undergo some deformation under stress. An object is condidered rigid in an application if its deformation is sufficiently small to be considered negligible when acted on by even the largest stresses expected to be encountered in that application. Accordingly, a splint is regarded as rigid while in service (worn on the limb) if it can withstand the stresses that a splint is normally expected to experience with acceptably small deformation.

It is desirable for the splint to be reshapable by bending so it can be adjusted by bending to fit the limb. A splint that is adjustable by bending should not be made of materials that are too brittle or too elastic. Many metals have the desired properties needed to be sufficiently rigid in service but bendable for adjustments.

Collar 17 is constructed as two cantilevers 64 and 65 (a cantilever is a structural part that is supported at one end by attachment to a relatively stationary object and is not supported at the other end). This construction enables collar 17 to be adjusted to fit hands over a wide range of sizes. The cantilever construction also enables the collar 17 to be bent into a helical shape. In this shape, collar 17 looks like an elongated letter C in end view as shown in FIG. 2, but looks like a letter S in top view as shown in FIG. 6. A collar of this shape oriented with a positive angle A turns out to be most comfortable for the right hand. A mirror-image configuration is most comfortable for the left hand.

Collar 17 is fabricated from an elongated stainless steel strip 23 (shown in FIG. 2) having a rectangular cross-section approximately ten millimeters wide by one millimeter thick (10 mm × 1 mm). The distal edge 62 of this strip is rolled to provide increased rigidity which is needed for the cantilever construction and to provide a comfortable edge in contact with the hand.

The sheet 15 has an attachment plate 512 at the distal end. The remaining parts of sheet 15 are made of stainless steel strips 24 having rectangular cross-sections approximately six millimeters wide by one millimeter thick (6 mm × 1 mm). Plate 512 is also 1 mm thick stainless steel. Sheet 15 is formed by first arranging the intersecting stainless steel strips 24 and plate 512 into a planar pattern similar to the one shown in FIG. 7. The strips 24 and plate 512 are spotwelded together at all positions of intersections 71 to yield a flat preform 72. This preform 72 is then bent into the shape of a part of a cone having a vertical angle of approximately 10 degrees. The distal end of the preform 72 is bent up so the points 73 and 75 move into contact with the points 74 and 76 respectively, and are spot-welded together at these contact points. Some of the welds 27 are shown in FIG. 2. Finally sheet 15 is deburred in a tumbling machine. After deburring, the sheet 15 has a smooth surface like fine jewelry.

By using mostly straight strips of stainless steel and doing most of the spot-welding on a plane, the cost of manufacture is minimized. The two final spot-welds which are done out of the plane of the preform 72 enable fabrication of sheet 15 into a shape that fits the forearm and the wrist much better than possible with other sheets having shapes that are formed from a planar surface by bending without stretching (many splints in the prior art are restricted to such latter shapes).

The cross-bracing elements 711–714 help improve the uniformity of stress-distribution over the splint 10; however, a splint without these elements would still function.

The practical limit of dimensions for the stainless-steel strips 24 are 0.7–3.0 mm thick, and 3.0–10.0 mm wide. If the strips are too thin or too narrow, then they are too weak; if they are too thick, then they are too heavy; if they are too wide, then removal of water from under them would be difficult.

There is one area of the wrist that is particularly sensitive to irritation by physical contact with hard surfaces. That sensitive area is the ulna prominence 111 which is shown in FIG. 1. The ulna is one of the long bones in the forearm extending from the elbow to the wrist. The distal ends of this bone extends outwards as a bump at the wrist. That is the ulna prominence 111 and it can be seen on most person's wrists. The bone here is not cushioned by very much soft tissue and is therefore easily irritated by contact with hard surfaces. To avoid irritation at the ulna prominance, The sheet 15 has two big holes 25 and 26 over the wrist area (shown in FIG. 2). When the splint 10 is worn over the right wrist, then the ulna prominence 111 is positioned in hole 25; and when a splint according to the present invention is worn over the left wrist, then the ulna prominence is positioned in hole 26.

The collar 17, stem 19, ring 110, and bridge 523 are all punched and formed by methods familiar to the art of metal stamping. They are also tumbler deburred. The screws 52, 53, 521 and 522 are spotwelded on after deburring.

As an alternative to the retainer means 12 used at the proximal end of splint 10, as shown in FIG. 1, a proximal collar 51 can be rigidly attached to the splint 50 as shown in FIG. 5. The collar 51 has buckles 529 and 530 that enable adjustments of collar 51 to fit forearms within a wide range of sizes. Wrist splints with adjustable proximal collars are more convenient and more comfortable than splints without, however, they are also more costly to manufacture.

The splint 80 in FIG. 8 has a rigid sheet 81 similar to sheet 15 of FIG. 1, but instead of collar 17, splint 80 has a glove 82 to prevent lateral motion of the hand relative to the sheet 81. Lateral motions of the wrist 83 and forearm 84 are prevented by retainer means 85 and 86 respectively.

FIGS. 9 and 10 show a splint 90 for use with retainer means 101 and 102 for restraining an ankle 100 against bending motions in the left-right directions. The splint 90 comprises a sheet 91 formed of stainless steel strips 92 similar to the construction of sheet 15. It has a big hole 93 for the bone prominence 103 at the ankle. The lower end of the sheet 91 is attached to a collar 94 which hooks around the bottom of the foot. Splint 90 can be worn with its lower extremity 95 inside a shoe 105 thus using the shoe to prevent left-right motion of the foot relative to the ankle 100 and lower leg 106.

FIG. 11 shows a splint 112 for use with retainer means 113 and 114 to immobilizing an ankle 115. Splint 112 comprises a rigid sheet 116 and a collar 117 having cantilever construction.

A well-fitted splint according to the present invention, when used with snugly fitted retainer means, can be more effective than a plaster or fiberglass cast for the purpose of immobilizing a part of a limb because the cast must be made to fit loosely to allow for natural changes in the size of the limb, whereas the retainer means can be wrapped snugly and can be readjusted when necessary.

A splint according to the present invention is comfortable to wear without padding material. If the splint or the underlying skin should become wet, they can be wiped dry with moisture-absorbing means (such as a towel or tissue paper). The limb and the splint can be cleaned by washing.

The many adjustments offered by a splint according to the present invention allow the physician to keep a relatively small inventory of splint parts and yet have splints to fit limbs of most sizes and shapes.

Stainless steel 304 is an excellent material for construction of splints of the types illustrated. However the present invention is not limited to the use of stainless steel. Other metals or plastics may also be used for construction of such splints.

In some applications, it may be desirable to have the sheet 15 formed by other methods besides welding together strips of metals. Also other adaptations of the present invention can be used to immobilize other parts of the limb. Such adaptations would be obvious to persons skilled in the art. They are not outside the scope of the present invention which is limited only by the claims below.

What is claimed is:

1. A splint to immobilize part of a limb; said splint comprising a rigid sheet, a rigid collar, and at least one retainer means;
   said sheet being formed into a shape to conform to the surface of one side of the limb;
   said sheet being formed of a plurality of intersecting metal strips that are welded together at the positions of intersection;
   said collar being rigidly attached to an extremity of said sheet;
   said collar being shaped like a letter "C", extending circumferentially more than halfway around said limb;
   said collar being operative to grip the limb and prevent all lateral motion of the limb relative to said sheet.

2. A splint according to claim 1 wherein said collar extends circumferentially more than two-thirds of the way around said limb.

3. A splint to immobilize part of a limb and a digit thereof comprising:
   a rigid sheet, at least one retainer means, a rigid collar, a stem, a ring, and a plurality of connecting means for connecting the stem to the collar;
   said sheet being formed into a shape to conform to the surface of one side of the limb;
   said collar being rigidly attached to an extremity of said sheet;
   said collar extending circumferentially more than halfway around said limb whereby said collar grips the limb to prevent lateral motion of the limb relative to said sheet;
   said stem having two extremities, one said extremity being rigidly connected to said ring and the other said extremity being rigidly connected to said collar;
   said ring being adapted to extend circumferentially more than halfway around the digit whereby said ring can grip said digit to prevent lateral motion of said digit relative to said collar;
   at least one said connecting means being carried by said collar and at least one other connecting means being carried by an extremity of said stem; the stem being connected to the collar by fastening together the respective connecting means.

4. A splint to immobilize part of a limb and a digit thereof;

said splint comprising a rigid sheet, a rigid collar, at least one retainer means, a ring and a stem;

said sheet being formed into a shape to conform to the surface of one side of the limb;

said sheet being formed of a plurality of intersecting metal strips that are welded together at the positions of intersection;

said collar being rigidly attached to an extremity of said sheet;

said collar extending circumferentially more than halfway around said limb whereby said collar grips the limb to prevent lateral motion of the limb relative to said sheet;

said stem having two extremities, one said extremity being rigidly connected to said ring and the other said extremity being rigidly connected to said collar; said ring being adapted to extend circumferentially more than halfway around the digit whereby said ring can grip said digit to prevent lateral motion of said digit relative to said collar.

* * * * *